United States Patent [19]

Yu et al.

[11] Patent Number: 5,169,868
[45] Date of Patent: Dec. 8, 1992

[54] ALIPHATIC PROPARGYLAMINES AS SPECIFIC MAO-B INHIBITORS

[75] Inventors: Peter H. Yu; Bruce A. Davis; Alan A. Boulton, all of Saskatoon, Canada

[73] Assignee: University of Saskatchewan, Saskatchewan, Canada

[21] Appl. No.: 663,018

[22] Filed: Mar. 1, 1991

[51] Int. Cl.$^5$ .............................................. A61K 31/13
[52] U.S. Cl. ................................ 514/671; 514/672; 564/509; 564/510
[58] Field of Search ............... 564/509, 510; 514/671, 514/672

[56] References Cited

U.S. PATENT DOCUMENTS

| | | | |
|---|---|---|---|
| 2,997,442 | 8/1961 | Tedeschi et al. | 167/65 |
| 3,000,903 | 9/1961 | Biel | 260/340.5 |
| 4,201,725 | 5/1980 | Pigerol et al. | 260/583 H |
| 4,650,907 | 3/1987 | Bey et al. | 564/509 |

FOREIGN PATENT DOCUMENTS 1453844 9/1966 France.

OTHER PUBLICATIONS

Boissier et al., Chimie Therapeutique, 1966, 320-326.
Boissier et al., Therapie, XXII, 1967, 367-373.
Neuromethods, vol. 5, Chapter 7, Neurotransmitter Enzymes, 1986, Humana Press.
Youdim et al, 1991, Biochemical Pharmacology, vol. 41, No. 2, pp. 133-162.
J. Pharm. Pharmacol. 1989, 41:205-208.
CA 67(13):63889(a) Boissier et al. 1966.

Primary Examiner—Richard J. Raymond
Assistant Examiner—B. M. Burn
Attorney, Agent, or Firm—Larson and Taylor

[57] ABSTRACT

A component having the following formula I:

$$CR''_3(CR'_2)_x\overset{R_1}{\underset{R_2}{C}}-N\overset{(CH_2)_y CH_3}{\underset{(CH_2)_z C\equiv CR_3}{}} \quad I$$

wherein
X represents an integer ranging from 1 to 2 or 7 to 13;
Y represents an integer ranging from 0 to 5;
Z represents an integer ranging from 0 to 5;
$R_1$, $R_2$ and $R_3$ are the same or different and represent H or a straight chain or branched lower alkyl; and
R' and R" are the same or different and represent H or halogen, and pharmaceutically acceptable salts thereof. Preferably, the lower alkyl has between 1 and 4 carbon atoms and the halogen is selected from the group consisting of fluorine, chlorine, bromine and iodine. The compound is useful as a MAO-B inhibitor. Also within the scope of the present invention is a composition for the inhibition of MAO-B activity and a method for alleviating Parkinsonism, Alzheimer's disease, depression, attention deficit hyperactive disorders, aging and other neuropsychiatric disorders and for improving the quality of life. They comprise the use of a compound of Formula I wherein x is an integer ranging from 1 to 13.

12 Claims, No Drawings

ALIPHATIC PROPARGYLAMINES AS SPECIFIC MAO-B INHIBITORS

FIELD OF THE INVENTION

The invention relates to a series of aliphatic propargylamines, their salts, formulations containing such compounds and to the use of such compounds as selective monoamine oxidase B inhibitors in human and veterinary medicine.

BACKGROUND OF THE INVENTION

Monoamine oxidase (MAO) is an enzyme that oxidizes monoamine neurotransmitters and neuromodulators, as well as exogenous bioactive monoamines. It was first characterized by Hare in 1928 and was later called MAO by Zeller in 1938. Following the characterization of this enzyme, it was later discovered that its inhibition could have positive effects on psychiatric disorders such as depression.

Iproniazid, described in the late 1950's and used as a treatment for tuberculosis, was found to have mood-elevating properties. It was later shown to be a suitable MAO inhibitor and was used thereafter as an effective antidepressant. However, the drug had to be withdrawn from the U.S. market in the early 1960's because of the reports of hepatic toxicity and occasional hypertensive crises associated with its use. Still, the success of Iproniazid as an antidepressant stimulated pharmaceutical companies to search for new MAO inhibitors having antidepressant properties without adverse side effects. Since then, a large number of MAO inhibitors have been synthesized and administered.

Until 1972, when it was discovered for the first time that MAO existed in two forms, namely MAO-A and MAO-B, the first generation of MAO inhibitors had no selective inhibitory activity towards MAO-A and/or MAO-B. Examples of these compounds are the drugs phenelzine and tranylcypromine, respectively patented in 1959 (U.S. Pat. No. 3,000,903) and 1961 (U.S.Pat. No. 2,997,422). Apart from inhibiting the activity of both MAO-A and MAO-B, these non-selective irreversible MAO inhibitor antidepressants also exhibit other important drawbacks. Hence, these drugs have been categorized as "dirty" drugs. In other words, they also block other enzymes and most importantly, they can, similarly to Iproniazid, cause severe hepatotoxicity and hypertension resulting from the ingestion of tyramine-rich food and drinks. This is caused by the fact that dietary amines are not broken down after ingestion and thus release circulating catecholamines which may lead to hypertensive crises and sometimes death. Thus, non-selective MAO inhibitors of this type have acquired a bad reputation and although they are very effective antidepressants, they have been avoided by most psychiatrists in favour of the relatively safer tricyclic antidepressants.

In the mid 1960's, a French group headed by Jacques R. Boissier published data on the synthesis of three series of new aliphatic and cycloaliphatic derivatives of hydrazine, propargylamine and cyclopropylamine, suspected to be useful as monoamine oxidase inhibitors (Chimie Therapeutique (1966), 320–326). Boissier et al. suggested that these non-selective total MAO inhibitors might possess therapeutic properties for the treatment of depression or angina pain. In French Patent 1,453,844, N-propynylalkylamines having a linear or branched alkyl group of 7 to 9 carbon atoms on the amino moiety are described.

In a further 1967 publication (Therapie, XXII, 1967, 367–373), Boissier et al. reported the results of tests conducted with these compounds to evaluate their antidepressant activity. Based on the results obtained, Boissier et al. concluded that the aliphatic compounds of the propargylamine series were practically inactive in vivo, regardless of whether the amine was secondary or tertiary, and only moderately active in vitro. From these results, it seemed that a promising future could not be foreseen for aliphatic propargylamines as effective MAO inhibitors. Hence, research involving compounds of this type was completely abandoned after the 1965, '66 and '67 publications by Boissier et al. It turned out that most of the research done later on MAO inhibitors concentrated on aromatic compounds.

In the early 1970's, it gradually became apparent that MAO existed in multiple forms, namely MAO-A and MAO-B. These two types of enzymes have been found to be somewhat different from one another. They exhibit different substrate profiles, they respond differently to selective inhibitors, they are found in different cellular and subcellular locations and they are distributed differently between neuronal and non-neuronal structures. Recently, MAO-A and MAO-B have been shown to arise from different gene loci. MAO-A is located predominantly inside the neurones and is responsible for causing hypertensive crises. It preferentially deaminates and oxidizes 5-hydroxy-tryptamine. As for MAO-B, it is found mostly in glia and it preferentially oxidizes $\beta$-phenylethylamine.

The discovery of MAO-A and MAO-B was of major importance since it initiated the research that led to the synthesis of second generation MAO inhibitors. The second generation MAO inhibitors are compounds that irreversibly or reversibly inhibit either the A or the B form of the enzyme. Because both the antidepressant and hypertensive effects are considered to be related to the inhibition of MAO-A, drug companies have concentrated their efforts mainly in the development of MAO-A inhibitors. Clorgyline, Lilly 51641 and PCO were among the first selective MAO inhibitors for MAO-A to be discovered. All these compounds belong to the first category of second generation MAO inhibitors and form irreversible links with the A enzyme.

The reversible specific MAO inhibitors, which form the second category of second generation inhibitors, have recently attracted attention because of their potentially improved clinical properties. Included in this category are harmine, harmaline, cimoxatone, brofaromine, amiflamine and moclobemide.

In recent years, a MAO-A inhibitory prodrug has also been discovered. MDL-72394 can be decarboxylated by aromatic L-amino acid decarboxylase and forms a potent irreversible MAO-A inhibitor, which has been shown to be neuronal selective. The chemical structures of first and second generation aromatic MAO-A and -B inhibitors may be found in Chapter 7 of Neuromethods, Volume 5, Neurotransmitter Enzymes, 1986, Humana Press, the contents of which is hereby incorporated by reference.

Research on MAO-B inhibitors is nowhere near the level of research accomplished so far for MAO-A. In fact, only a few irreversible MAO-B inhibitors such as Deprenyl and Pargyline have so far been discovered. Deprenyl is one of the most important and widely tested MAO-B inhibitors. It has been used as an effective adjuvant to L-DOPA in the treatment of Parkinson's disease. The combination of Deprenyl and L-DOPA seems to reduce the requirement for L-DOPA (presently known to be the best antiparkinsonian agent) in those cases where L-DOPA is being ingested. Recently, it was reported that Deprenyl alone can significantly delay the onset of disability associated with early, otherwise, untreated cases of Parkinson's disease. It has also been claimed that the use of Deprenyl improved the clinical condition of some Alzheimer's patients and reduced depression, attention deficit disorders and potentially other neuropsychiatric disorders. In addition, Deprenyl has been observed to prolong life span and sexual activity in animals and humans. Unlike MAO-A inhibitors, MAO-B inhibitors do not usually cause hypertensive crises except, in some instances, under chronic large-dose applications and therefore have the potential to become very useful neuropsychiatric and geriatric drugs.

Although Deprenyl at higher doses can cause a slight increase in dopamine levels in the brain, the involvement of dopamine in the mechanism of action of Deprenyl has not been well established. The inhibition of MAO-B activity causes a selective accumulation of β-phenylethylamine, a typical MAO-B substrate, which is present endogenously, including in the central nervous system. β-Phenylethylamine, which possesses stimulant properties, can amplify dopaminergic function and modulate dopaminergic neurotransmission and is therefore related to the chemotherapy of MAO-B inhibitors.

It was also found that since Deprenyl is a structural analog of amphetamine, it is catabolized to produce small amounts of amphetamine. This has caused some concern because it was hypothesized that Deprenyl might, in some instances, be a drug subject to substance abuse. Hence, different MAO-B inhibitors not possessing amphetamine-like properties are required. Recently, the reversible MAO-B inhibitors MD 780236 and RO-16-6491 as well as the irreversible inhibitor MDL-72145 were discovered but other alternatives are still being sought. Recent studies on currently available MAO-A and MAO-B inhibitors are summarized in Youdim et al., (1991) Biochemical Pharmacology, Vol. 41, No. 2, pp. 133-162, which is hereby incorporated by reference.

In 1989, the results of a systematic investigation on the deamination by MAO-A and -B of amines having aliphatic chains of various lengths were published (J. Pharm. Pharmacol. 1989, 41:205-208). It was found that these amines were readily oxidized by MAO-B with very high affinity. The deamination of these aliphatic amines by MAO-B was found to be even more sensitive to Deprenyl than that of β-phenylethylamine, which is known to be a typical MAO-B substrate. Unfortunately, although these compounds were found to be good substrates for MAO-B, they did not exhibit any inhibitory activity towards this enzyme.

In summary, active research on MAO inhibitors has been carried out since as early as 1950 and hundreds of potentially useful MAO inhibitors have been synthesized. There was an important change in research focus in the early 1970's when the existence of two different forms of MAO enzymes was discovered. It seems that substantial progress has been made in MAO-A inhibition but much more work remains to be done to find suitable MAO-B inhibitors. Since the inhibition of MAO-B appears to alleviate the symptoms of aging associated diseases such as Parkinson's disease and Alzheimer's disease, suitable MAO-B inhibitors would be highly desirable, especially in view of the limited and relatively inefficient treatments available for these diseases.

SUMMARY OF THE INVENTION

The present invention relates to a compound having the following formula I:

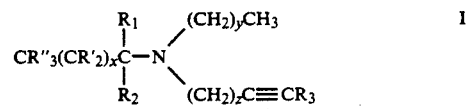

wherein
x is an integer ranging from 1 to 2 or 7 to 13;
y is an integer ranging from 0 to 5;
z is an integer ranging from 0 to 5;
$R_1$, $R_2$ and $R_3$ are the same or different and represent hydrogen or a straight chain or branched lower alkyl; and
R' and R" are the same or different and represent H or halogen,
and pharmaceutically acceptable salts thereof.

Preferably the lower alkyl has between 1 and 4 carbon atoms and the halogen atom is selected from fluorine, chlorine, bromine and iodine. More preferably, the lower alkyl is selected from methyl.

The compounds of the present invention have been found to be highly potent, irreversible, selective MAO-B inhibitors. These novel MAO-B inhibitors are characterized by having a chemical structure that is not amphetamine-like. They can therefore block MAO-B activity but without any amphetaminergic effect. The compounds of the present invention may be used in the treatment of various neuropsychiatric disorders in humans or animals, such as Parkinsonism, Alzheimer's disease, depression, attention deficit disorders, hyperactive disorders, aging and to improve the quality of life in humans or animals.

Aliphatic propargylamines with short (x=1 to 2) or long (x=7 to 13) carbon chain lengths have been found to be unexpectedly efficient in inhibiting MAO-B activity. It seems that the compounds with short aliphatic chains are less easily absorbed and more readily transported into the brain and could therefore be more effective in blocking MAO-B activity following oral administration.

It has also been found that aliphatic propargylamines with short carbon chain lengths are less effective MAO-B inhibitors in vitro but become significantly more active when they are administered peripherally and especially after oral ingestion. Such in vitro and in vivo data indicate that the pharmacokinetic properties of the short chain aliphatic MAO-B inhibitors are distinctly different from those of the longer aliphatic propargylamines and Deprenyl. This aspect is particularly desirable in clinical applications.

With regard to the long carbon chain propargylamines, although they appear to be less potent at inhibiting MAO-B activity after acute administration, and this perhaps may be due to increased absorption, they are slowly released thereafter and may thus be useful from a chronic treatment point of view.

Another worthwhile aspect to note is that the selectivity of some of these compounds towards MAO-B is significantly higher than for Deprenyl. This is very important since it reduces or eliminates any possible hypertensive effects even after chronic treatment.

The present invention also relates to a pharmaceutical composition for inhibiting MAO-B activity. The composition comprises an effective amount of a compound having the following formula I:

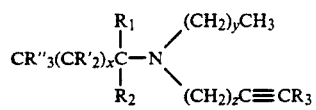

wherein
x is an integer ranging from 1 to 13;
y is an integer ranging from 0 to 5;
z is an integer ranging from 0 to 5;
$R_1$, $R_2$ and $R_3$ are the same or different and represent hydrogen or a straight chain or branched lower alkyl; and
R' and R" are the same or different and represent H or halogen,
and pharmaceutically acceptable salts thereof, in admixture with a pharmaceutically acceptable carrier, excipient or adjuvant.

Preferably, the lower alkyl has between 1 and 4 carbon atoms and the halogen atom is selected from fluorine, chlorine, bromine and iodine. More preferably, the lower alkyl is selected from methyl.

The compositions described above have been found to be potent selective and irreversible MAO-B inhibitors. These findings are unexpected, especially in view of the comments of Boissier et al. in Therapie XXII, 1967, 367-373. Boissier et al. had found aliphatic propargylamines to be practically inactive in vivo regardless of whether the amine is secondary or tertiary and only moderately active in vivo. As mentioned previously, it has been found that the compounds with aliphatic chains shorter (x=1 to 2) and longer (x=7 to 13) than those described by Boissier et al. are the most useful ones from a pharmacological standpoint.

The present invention also relates to a method for alleviating neuropsychiatric disorders such as Parkinsonism, Alzheimer's disease, depression, attention deficit disorders, hyperactive disorders, aging and to improve the quality of life in humans or animals. The method comprises administering to a subject suffering from a neuropsychiatric disorder an effective amount of the compound having the following formula I:

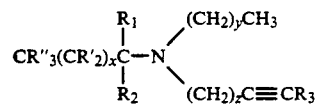

wherein
x is an integer ranging from 1 to 13;
y is an integer ranging from 0 to 5;
z is an integer ranging from 0 to 5;
$R_1$, $R_2$ and $R_3$ are the same or different and represent hydrogen or a straight chain or branched lower alkyl; and
R' and R" are the same or different and represent H or halogen,
and pharmaceutically acceptable salts thereof, in admixture with a pharmaceutically acceptable carrier, excipient or adjuvant.

Preferably, the lower alkyl has between 1 and 4 carbon atoms and the halogen atom is selected from fluorine, chlorine, bromine and iodine. More preferably, the lower alkyl is selected from methyl.

The present invention also relates to a method of veterinary treatment to prolong life span and to reduce or obviate neurological or age-related disorders. The method comprises administering to an animal an effective amount of the compound according to the following formula I:

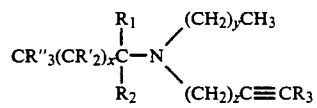

wherein
x is an integer ranging from 1 to 13;
y is an integer ranging from 0 to 5;
z is an integer ranging from 0 to 5;
$R_1$, $R_2$ and $R_3$ are the same or different and represent hydrogen or a straight chain or branched lower alkyl; and
R' and R" are the same or different and represent H or halogen,
and pharmaceutically acceptable salts thereof, in admixture with a pharmaceutically acceptable carrier, excipient or adjuvant.

Preferably, the lower alkyl has between 1 and 4 carbon atoms and the halogen atom is selected from fluorine, chlorine, bromine and iodine. More preferably, the lower alkyl is methyl.

Also within the scope of the present invention is a process for preparing a compound having the following formula I:

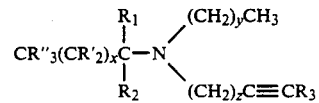

The process comprises condensing an alkyl bromide with N-methylpropargylamine in the presence of a base and recovering the desired compound.

The present invention will be more readily illustrated by referring to the following description.

DETAILED DESCRIPTION OF THE INVENTION

Synthesis of the compounds

The compounds used in the context of the present invention can be prepared by condensing the appropriate alkyl bromides with N-methylpropargylamine in the presence of a base. Preferably, the base may be either an extra equivalent of N-methylpropargylamine or anhydrous sodium carbonate according to the following reaction schemes.

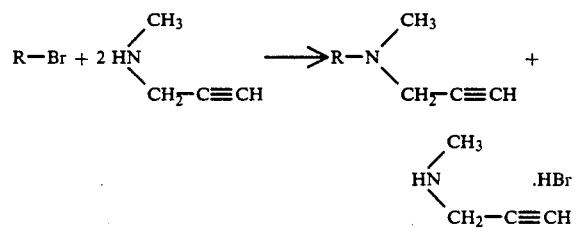

or

-continued

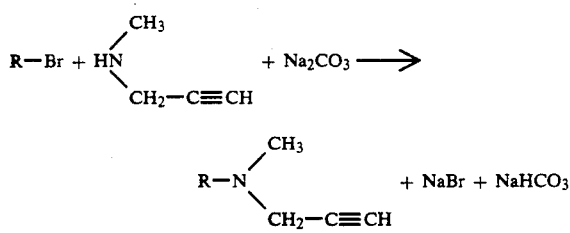

The former reaction is more convenient but more expensive. Any unreacted N-methylpropargylamine (b.p. 82°-84° C.) is readily removed during distillation of the solvent and in the water wash (solubility in water is infinite). The reaction may be carried out in ethanol, methanol, acetone, toluene, benzene or any solvent possessing similar properties, especially with regard to convenience of removal, evaporation and the like. Satisfactory yields were obtained when absolute ethanol was used. Hence, one of the interesting advantages of this method resides in the fact that methylpropargylamine has a low boiling point and is therefore easy to remove. Also, N-methylpropargylamine is soluble in water and therefore the clean-up is relatively simple.

The yields of the propyl, butyl and pentyl analogs are relatively low due to the volatility of the free bases (some loss occurs during removal of solvent) and to their slight to moderate solubility in water (further loss occurs during the water wash to remove N-methylpropargylamine hydrobromide and excess free base N-methylpropargylamine).

Alternatively, the compounds of the present invention may be prepared following the general procedure described in French Patent 1453844, issued Aug. 22, 1966 or in Boissier et al. (1966), Chimie Therapeutique, 320-326, which are hereby incorporated by reference. Finally and preferably, the compounds can also be prepared starting from a 2-aminoalkane, which is methylated via reaction with methyl chloroformate followed by reduction of the resulting carbamate with lithium aluminium hydride in ether. Without isolation of the N-methylalkylamine from the final ether solution, reaction with propargyl bromide with sodium carbonate as a base yields the desired N-2-alkyl-N-methylpropargylamine, isolated as its salt, preferably the hydrochloride or oxalate salt.

It may be desirable to prepare a specific isomeric form of one of the compounds of the present invention, as particular isomers are thought to possess even more potent MAO-B inhibitory activity than the racemic mixtures. As an illustrative example, (+) or (−)-2-butylamine is reacted with methylchloroformate and the resulting product (a carbamate) is reduced with lithium aluminum hydride to produce (+) or (−) N-methyl-2-butylamine. The formed methyl compound, still in the ether solution from the previous step, may then be directly reacted with propargyl bromide and sodium carbonate without requiring previous isolation or purification. The final ethereal reaction mixture is then filtered and washed with water to remove the remaining reagents and then dried. The desired compound, which is still dissolved in ether, is then added to a suitable acid such as oxalic acid to yield the final product as a salt which can be recrystallized from a solvent or solvent mixture such as methanol/ether if required. Any competent chemist will appreciate that any reagent used in this process may be replaced by another compound performing the same function.

HCl salts can be prepared for all members of the series following procedures which are well-known to those skilled in synthetic chemistry. In the case of the propyl, butyl and pentyl analogs, the HCl salts appear to be difficult to re-crystallize but the oxalate salts, which crystallize readily, can be alternatively prepared. With regard to the hydrochlorides of the longer alkyl chain analogs, they crystallized without difficulty. It is to be understood by the skilled chemist that salts such as sulphates, tartrates, benzoates, hydrobromides and the like can also be prepared. In fact, the appropriate choice of the type of salt may be useful to impart further advantages to the analogs of the present invention such as lowering solubility or causing slower release.

Structural identity of the described compounds can be ascertained by mass spectrometry and elemental analysis. The mass spectra of all the compounds are characterized by a small molecular ion (typically less than 10% relative intensity) and a base peak (relative intensity 100%) arising by bond cleavage of the alkyl chain alpha to the nitrogen atom.

The present invention will be more readily illustrated by referring to the following examples. Except for N-(2-heptyl)-N-methylpropargylamine, all the compounds described in these examples were synthesized for the first time.

EXAMPLE 1

N-(2-Butyl)-N-methylpropargylamine hydrochloride and oxalate (2-BuMPP).

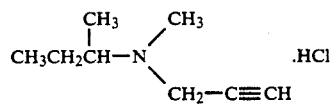

A solution of 2-bromobutane (6.86 g, 50 mmoles) in absolute ethanol (5 mL) was added to a gently refluxing solution of N-methylpropargylamine (3.46 g, 50 mmoles) in absolute ethanol (45 mL) containing powdered anhydrous sodium carbonate (5.3 g, 50 mmoles). After stirring under gentle reflux for 72 h, the mixture was allowed to cool, then was filtered and 45 mL of ethanol was distilled off. The residue was diluted with 75 ml of ethyl ether and washed with 2×20 mL water. The ethereal solution was dried over anhydrous magnesium sulfate and filtered. The filtrate was then diluted to 150 mL with ether and treated with ethanolic hydrochloric acid (prepared by the addition of 50 mmoles of acetyl chloride to 10 mL of ice-cold absolute ethanol). The initial, rapid precipitation was an oil which very slowly crystallized; white needles subsequently very slowly precipitated from the supernatant. Overall yield was 35%, m.p. 150°-151° C.:

Elemental analysis: $C_8H_{16}ClN$:
Calculated: C=59.43% H=9.98% N=8.66%
Found: C=59.60% H=10.11% N=8.51%
Mass spectrum: $M^+ = 125$ (4%), base peak m/e=96, $M-CH_3$=m/e 110 (15%).

The oxalate salt was readily formed by the addition of the ethereal solution of the free base (prepared as described above) to a stirred solution of oxalic acid (4.5 g, 50 mmoles) in anhydrous ether (500 mL). Yield was 34%, m.p. 123°-124° C.:

Elemental analysis: $C_{10}H_{17}NO_4$:

Calculated: C=55.80% H=7.96% N=6.51%
Found: C=55.93% H=7.86% N=6.64%.

Similar yields of the title compound were obtained when an extra 50 mmoles of N-methylpropargylamine were used as base instead of anhydrous sodium carbonate.

EXAMPLE 2

Alternate method for the preparation of N-(2-butyl)-N-methylpropargylamine oxalate.

A solution of 2-aminobutane (5.0 g, 68 mmoles), 4-dimethylaminopyridine (850 mg, 7 mmoles) and triethylamine (8.4 g, 83 mmoles) in dichloromethane (150 mL) was cooled in an ice-water bath and treated dropwise with methyl chloroformate (7.05 g, 75 mmoles). After one hour, the reaction mixture was diluted with dichloromethane (150 mL) and washed successively with water (80 mL), 0.1N HCl (2×80 mL) and water (80 mL), then dried over anhydrous sodium sulfate. Removal of the solvent gave 9.0 g (100%) of product as a pale yellow oil which was reduced by addition to a suspension of lithium aluminum hydride (3.6 g, 95 mmoles) in ether (185 mL). Following gentle reflux for two hours, the product was isolated in ether by the careful addition of water (3.6 mL), 10% NaOH (3.6 mL) and water (10 mL) and filtration. The ether solution was dried over anhydrous magnesium sulfate then treated with propargyl bromide (8.1 g, 68 mmoles) and sodium carbonate (7.2 g, 68 mmoles). The mixture was gently refluxed for 24 hours, then filtered. The product was isolated as the oxalate salt by addition of the filtrate to a stirred solution of oxalic acid (6.1 g, 68 mmoles) in ether (250 mL). The precipitate was filtered with suction and dried (6.0 g) (41% overall yield). (m.p.=124°-125° C.).

This procedure can be used to prepare the two stereoisomers of the product since (R)-2-aminobutane and (S)-2-aminobutane are commercially available.

EXAMPLES 3-10

The process used in Example 1 was also used for the preparation of the compounds described in Examples 3-10. However, where methylpropargylamine base or Na$_2$CO$_3$ are used, it is important if using Na$_2$CO$_3$ to filter it off before continuing the synthesis. This is not a problem when using N-methylpropargylamine although in this case, it is necessary to wash away the excess reagent with water.

EXAMPLE 3

N-(1-Butyl)-N-methylpropargylamine hydrochloride (1-BuMPP).

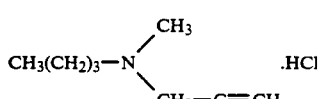

1-Bromobutane (6.86 g, 50 mmoles), N-methylpropargylamine (3.46 g, 50 mmoles) and anhydrous sodium carbonate (5.3 g, 50 mmoles) heated for 72 h. in absolute ethanol gave a 52% yield of the title compound after recrystallization from methanol-ether, m.p.=144°-145° C. The same compound in approximately the same yield was obtained when 1-bromobutane (50 mmoles) and N-methylpropargylamine (100 mmoles) were gently refluxed for 72 h. in absolute ethanol.

Elemental analysis: C$_8$H$_{16}$ClN: Calculated: C=59.43% H=9.98% N=8.66% Found: C=59.69% H=9.94% N=8.77%

Mass spectrum: M$^+$=125 (4%), base peak m/e=82, M—CH$_3$=m/e 110 (8%).

EXAMPLE 4

N-(2-Propyl)-N-methylpropargylamine hydrochloride (MPPP).

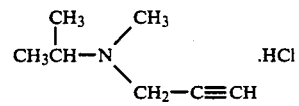

2-Bromopropane (3.08 g, 25 mmoles) and N-methylpropargylamine (3.45 g, 50 mmoles) in absolute ethanol (50 mL) were heated at reflux for 48 h. On treatment of the ethereal solution of the free base with ethanolic hydrochloride acid, an oil first separated, and then white needles subsequently precipitated very slowly from the supernatant (16% yield of white needles, recrystallized from methanol-ether), m.p.=155°-156° C. The oil and the needles gave identical mass spectra.

Elemental analysis: C$_7$H$_{14}$ClN: Calculated: C=56.94% H=9.56% N=9.49% Found: C=57.07% H=9.63% N=9.52%

Mass spectrum: M$^+$=111 (10%), base peak m/e=96.

EXAMPLE 5

N-(1-Pentyl)-N-methylpropargylamine oxalate (M-1-PPP).

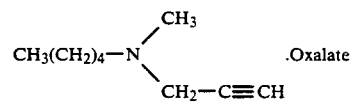

1-Bromopentane (12.1 g, 80 mmoles) and N-methylpropargylamine (11.1 g, 160 mmoles) were refluxed in absolute ethanol (75 mL) for 72 h. to give (after addition to 80 mmoles of oxalic acid in ether) the title compound in 60% yield after recrystallization from methanol-ether, m.p.=101°-103° C.

Elemental analysis: C$_{11}$H$_{19}$NO$_4$: Calculated: C=57.63% H=8.35% N=6.11% Found: C=57.72% H=8.29% N=5.92%

Mass spectrum: M$^+$=139 (3%), base peak m/e=82.

EXAMPLE 6

N-(2-Pentyl)-N-methylpropargylamine hydrochloride and oxalate (M-2-PPP).

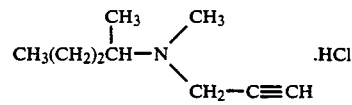

2-Bromopentane (12.1 g, 80 mmoles) and N-methylpropargylamine (11.1 g, 160 mmoles) were heated at reflux for 48 h. in absolute ethanol (50 mL). The hydrochloride salt precipitated from ether as an oil which did not crystallize (yield=63%).

Mass spectrum: M$^+$=139 (6%), base peak=m/e 96, M—CH$_3$=m/e 124 (21%).

The oxalate salt (yield 50%), from free base prepared as above, was recrystallized from methanol-ether, m.p. 89°-90° C.

Elemental analysis: $C_{11}H_{19}NO_4$: Calculated: C=57.63% H=8.35% N=6.11% Found: C=57.58% H=8.22% N=6.01%

Mass spectrum: $M^+$=139 (4%), base peak=m/e 96, $M-CH_3$=124 (22%).

EXAMPLE 7

N-(1-Heptyl)-N-methylpropargylamine hydrochloride (1-HMPP).

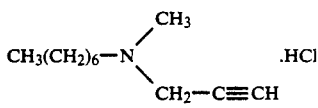

1-Bromoheptane (3.58 g, 20 mmoles) and N-methylpropargylamine (2.76 g, 40 mmoles) were refluxed in absolute ethanol for 24 h. The product separated immediately on treatment with ethanolic HCl as medium-brown crystals in a yield of 100% (84% as white crystals after recrystallization from methanol-ether), m.p.=124°-125° C.

Elemental analysis: $C_{11}H_{22}ClN$: Calculated: C=64.84% H=10.88% N=6.87% Found: C=64.97% H=10.78% N=6.92%

Mass spectrum: $M^+$=167 (18%), base peak=m/e 82, $M-[C-CH]$=m/e 142 (15%).

EXAMPLE 8

N-(2-Heptyl)-N-methylpropargylamine hydrochloride (2-HMPP).

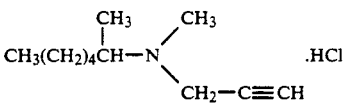

2-Bromoheptane (7.16 g, 40 mmoles) and N-methylpropargylamine (5.52 g, 80 mmoles) were gently refluxed for 24 h. in absolute ethanol (50 mL). Yield was 100% (66% after recrystallization from acetone-pentane), m.p.=115°-116° C.

Elemental analysis: $C_{11}H_{22}ClN$: Calculated: C=64.84% H=10.88% N=6.87% Found: C=65.01% H=10.93% N=6.95%

Mass spectrum: $M^+$=167 (5%), base peak=m/e 96, $M-CH_3$ (23%).

EXAMPLE 9

N-(2-Decyl)-N-methylpropargylamine hydrochloride (2-DMPP).

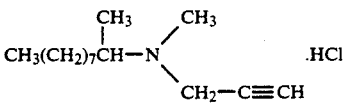

2-Bromodecane (8.84 g, 40 mmoles) and N-methylpropargylamine (5.52 g, 80 mmoles) were heated in absolute ethanol (50 mL) for 72 h. to give, after treatment with 40 mmoles of ethanolic hydrochloric acid, the title compound in a yield of 100% (75% after recrystallization from methanol-ether), m.p.=130°-131° C.

Elemental analysis: $C_{14}H_{28}ClN$: Calculated: C=68.40% H=11.48% N=5.70% Found: C=68.20% H=11.36% N=5.82%

Mass spectrum: $M^+$=209 (1), base peak=m/e 96, $M-CH_3$ (33%).

EXAMPLE 10

N-(2-Dodecyl)-N-methylpropargylamine hydrochloride (DdMPP).

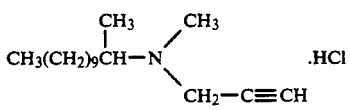

2-Bromododecane (5.3 g, 21 mmoles) and N-methylpropargylamine (3.45 g, 50 mmoles) were heated at reflux in absolute ethanol (50 mL) for 48 h. After treatment of the free base with ethanolic hydrochloric acid, the title compound was obtained in a yield of 30% after recrystallization from acetone-pentane, m.p.=128°-130° C.

Elemental analysis: $C_{16}H_{32}ClN$: Calculated: C=70.16% H=11.78% N=5.12% Found: C=70.28% H=11.80% N=5.03%

Mass spectrum: $M^+$=237 (0.05%), base peak=m/e 96, $M-CH_3$=m/e 222 (10%).

Inhibition of MAO activities in vitro

A radioenzymatic procedure was used for the estimation of MAO activities (Neuromethods V; Neurotransmitter enzymes, 1986, Humana Press, N.J.). MAO-A and MAO-B activities from rat liver mitochondrial membranes were assayed using 5-HT ($5 \times 10^{-4}$M) and PE ($5 \times 10^{-5}$M) as substrates respectively. The aliphatic propargylamine inhibitors (from $1 \times 10^{-10}$M to $1 \times 10^{-4}$M) were preincubated with the MAO for 20 min. at ambient room temperature and then the residual enzyme activities were determined by addition of the substrates, followed by further incubation at 37° C. for 30 min. The enzymatic reactions were terminated by the addition of citric acid and the aldehyde products were extracted with toluene: ethyl acetate (1:1, v/v) and the radio-activities assessed in a scintillation counter. The inhibitory activities ($IC_{50}$) of eight aliphatic propargylamines, towards MAO-B and MAO-A are summarized in Table 1. All of them are highly selective MAO-B inhibitors with MAO-A/MAO-B ratios of their $IC_{50}$ values ranging from 20 to 200. Compounds with longer carbon chain lengths are more active in the inhibition of MAO-B activity in vitro and some of them are more selective than Deprenyl. These compounds also actively inhibit the deamination of dopamine (DA), which is a mixed-type MAO (A and B) substrate.

TABLE 1

Inhibition of rat liver monoamine oxidase activities towards different substrates by some aliphatic propargylamines in vitro

| Inhibitors* | PE ($5 \times 10^{-5}$M) IC$_{50}$ | 5-HT ($5 \times 10^{-4}$M) IC$_{50}$ | Ratio MAO-A/MAO-B | DA ($5 \times 10^{-4}$M) IC$_{50}$ |
|---|---|---|---|---|
| MPP | $2 \times 10^{-5}$M | $>1 \times 10^{-4}$M | | $3 \times 10^{-5}$M |
| 1-BuMPP | $1 \times 10^{-6}$M | $1 \times 10^{-4}$M | 100 | — |
| 2-BuMPP | $1 \times 10^{-6}$M | $2 \times 10^{-5}$M | 20 | $5 \times 10^{-7}$M |
| M-2-PPP | $2 \times 10^{-7}$M | $1 \times 10^{-5}$M | 50 | $6 \times 10^{-6}$M |
| M-1-PPP | $4 \times 10^{-7}$M | $1 \times 10^{-4}$M | 200 | — |
| 2-HMPP | $2 \times 10^{-7}$M | $2 \times 10^{-5}$M | 100 | $3 \times 10^{-7}$M |
| 1-HMPP | $2 \times 10^{-6}$M | $4 \times 10^{-5}$M | 20 | — |
| 2-DMPP | $2 \times 10^{-7}$M | $4 \times 10^{-6}$M | 50 | $2 \times 10^{-7}$M |
| 2-DdMPP | $4 \times 10^{-8}$M | $2 \times 10^{-6}$M | 50 | $3 \times 10^{-7}$M |
| Deprenyl** | $5 \times 10^{-8}$M | $3 \times 10^{-6}$M | 60 | $3 \times 10^{-7}$M |

Results are the average of 3 independent experiments for each compound.
*MPP: N-(2-propyl)-N-methyl-N-propargylamine.HCl
2-BuMPP: N-(2-butyl)-N-methyl-N-propargylamine.HCl
1-BuMPP: N-(1-butyl)-N-methyl-N-propargylamine.HCl
M-2-PPP: N-(2-pentyl)-N-methyl-N-propargylamine.HCl
M-1-PPP: N-(1-pentyl)-N-methyl-N-propargylamine.Oxalate
2-HMPP: N-(2-heptyl)-N-methyl-N-propargylamine.HCl
1-HMPP: N-(1-heptyl)-N-methyl-N-propargylamine.HCl
2-DMPP: N-(2-decyl)-N-methyl-N-propargylamine.HCl
2-DdMPP: N-(2-dodecyl)-N-methyl-N-propargylamine.HCl
**Deprenyl is the L-isomer, while the aliphatic propargylamines were racemic.

Inhibition of MAO activities in viro

Albino Swiss mice were used in this study. The animals were injected intraperitoneally with different doses of the aliphatic propargylamines in 100 μL saline. The forebrains were dissected out, two hours after treatment, and MAO-A and MAO-B activities were estimated. In this study, aliphatic propargylamines with shorter carbon chain lengths (such as 2-BuMPP, 1-BuMPP, M-2-PPP and M-1-PPP appear to be more potent than the longer chain analogs at inhibiting brain MAO-B activity (see Table 2), indicating that these smaller molecules are less easily absorbed (e.g., into lipids, membranes, etc) and more readily transported into the brain. These shorter propargylamine MAO-B inhibitors were also more effective in blocking MAO-B activity in the brain following oral administration.

TABLE 2

MAO activities in the mouse brain after intraperitoneal administration of aliphatic propargylamine MAO inhibitors.

| Inhibitors* | PE ($5 \times 10^{-5}$M) ED$_{50}$ | 5-HT ($5 \times 10^{-4}$M) ED$_{50}$ | Ratio MAO-A/MAO-B | MAO-B ED$_{50}$ (mg/Kg) IC$_{50}$ ($1 \times 10^{-6}$M) |
|---|---|---|---|---|
| 2-BuMPP | 1 | 20 | 20 | 1 |
| 1-BuMPP | 2 | 100 | 50 | 2 |
| M-2-PPP | 0.5 | 25 | 50 | 2.5 |
| M-1-PPP | 2 | >100 | >50 | 5.0 |
| 2-HMPP | 0.5 | 25 | 50 | 2.5 |
| 1-HMPP | 15 | 100 | 7 | 7.5 |
| 2-DMPP | 5 | 35 | 7 | 25 |
| 2-DdMPP | 4 | 60 | 15 | 100 |
| Deprenyl | 0.5 | 25 | 50 | 10 |

Results are the average of 3 to 8 animals for each i.p. doses, i.e. 0.5, 1, 2, 5, 10, 20, 50, 100 mg/Kg, of the compounds. Forebrains were dissected two hours after i.p. administration of the drugs. MAO-A and MAO-B activities were determined immediately.
*IC$_{50}$ values and abbreviations are as described in Table 1.

Table 3 indicates the MAO activities in the mouse brain following oral administration of the aliphatic propargylamines. Short chain compounds clearly exhibit superior transport properties, since although they are moderately active in inhibiting MAO-B activity in vitro, they are much more active after oral administration in comparison to Deprenyl. The longer carbon chain propargylamines, i.e. 2-DMPP and 2-DdMPP, are less potent at inhibiting MAO-B activity in vivo after acute administration (perhaps due to increased absorption). This is perhaps caused by a slower release which could be useful from a chronic treatment point of view.

TABLE 3

MAO activities in the mouse brain after oral administration of aliphatic propargylamine MAO inhibitors (10 mg/kg).

| Inhibitors* | Relative activity (%) PE ($5 \times 10^{-5}$M) | 5-HT ($5 \times 10^{-4}$M) | number of mice |
|---|---|---|---|
| Saline | 100 | 100 | 6 |
| 2-BuMPP | 28 | 97 | 6 |
| 1-BuMPP | 67 | 98 | 3 |
| M-2-PPP | 31 | 89 | 3 |
| M-1-PPP | 72 | 97 | 3 |
| 2-HMPP | 39 | 99 | 6 |
| 1-HMPP | 118 | 123 | 3 |
| 2-DMPP | 104 | 97 | 3 |
| 2-DdMPP | 64 | 107 | 3 |
| Deprenyl | 40 | 99 | 6 |

Results are the average of 3 to 6 animals for an oral dose of 10 mg/Kg of each compound. Forebrains were dissected two hours after the administration of the drugs. MAO-A and MAO-B activities were determined immediately.
*Abbreviations are as described in Table 1.

Toxicity and hypertensive effect

The aliphatic propargylamines described above are not only highly potent and specific with respect to inhibition of MAO-B activity (Tables 1 to 3), they also do not possess an amphetamine-like residue within their structure. Thus, they represent a substantial improvement over already available MAO-B inhibitors and they cannot produce amphetaminergic side-effects, as a result of metabolic breakdown. Furthermore, because these compounds are highly selective MAO-B inhibitors, like Deprenyl, they will not cause the hypertensive reaction usually observed with MAO-A inhibitors.

The acute toxicity of these compounds is quite low. In toxicity studies performed with some of the compounds disclosed in the examples, namely 2-BuMPP 1-BuMPP, M-2-PPP and M-1-PPP, oral administration to mice at doses up to 1000 mg/kg resulted in no fatality. This is significantly less toxic than Deprenyl, for which the $LD_{50}$ has been reported to be 445 mg/kg. The aliphatic side-chains of these aliphatic propargyl compounds are similar to those that exist in endogenous lipids and fatty acids and such aliphatic chains are readily oxidized in vivo. The major metabolic products of Deprenyl are methamphetamine or amphetamine which probably arise by hydroxylation and cleavage between the propargyl and the amphetamine moieties. Aliphatic propargylamines are likely to be hydrolyzed in a similar manner. 1-BuMPP, for instance, would be hydrolyzed to n-butylamine, which is then deaminated to form n-butylaldehyde and subsequently oxidized to the totally non-toxic n-butyric acid.

Formulations and dosages

The compounds of the present invention can be used in human and veterinary therapy for the treatment of various diseases of the central nervous system and consequently a formulation could include all pharmaceutical compositions containing the aliphatic propargylamines referred to above as active principals, in association with any excipients which are suitable for their administration. In oral administration, the compounds may be administered as tablets, coated tablets, gelatine capsules, capsules, cachets, and solutions or suspensions to be taken orally. The compounds can also be administered parenterally or through any other suitable administrative route such as intravenous, subcutaneous, depot injections, intramuscular, intrathecal, intraventricular, intra-articular, rectal (suppository, enema), sublingual, buccal, intra-ocular, intra-vitreo, transdermal (this is the skin patch), nasal drops (nebuliser, infufflation), liposomal delivery systems. The daily dosages could likely range from 1 to 100 mg.

Claims to the invention follow.

We claim:

1. A compound having the following formula I: wherein
X represents an integer ranging from 1 to 2 or 7 to 13;
$R_2$ and $R_3$ are the same or different and represent H or a straight chain or branched lower alkyl;
R' and R" are the same or different and represent H or a straight chain or branched lower alkyl;
and pharmaceutically acceptable salts thereof.

2. A compound according to claim 1, wherein said lower alkyl has between 1 and 4 carbon atoms.

3. A compound according to claim 1, wherein said compound of formula I is selected from the group consisting of:
N-(2-butyl)-N-methylpropargylamine hydrochloride,
N-(2-butyl)-N-methylpropargylamine oxalate,
N-(1-butyl)-N-methylpropargylamine hydrochloride,
N-(2-propyl)-N-methylpropargylamine hydrochloride,
N-(1-pentyl)-N-methylpropargylamine hydrochloride,
N-(2-pentyl)-N-methylpropargylamine hydrochloride,
N-(2-pentyl)-N-methylpropargylamine oxalate,
N-(2-decyl)-N-methylpropargylamine hydrochloride, and
N-(2-dodecyl)-N-methylpropargylamine hydrochloride.

4. A composition for the inhibition of MAO-B activity comprising an effective amount of the compound having the following formula I:
wherein
X represents an integer ranging from 1 to 13;
$R_2$ and $R_3$ are the same or different and represent H or a straight chain or branched lower alkyl;
and pharmaceutically acceptable salts thereof, in admixture with a pharmaceutically acceptable carrier, excipient or adjuvant.

5. A composition according to claim 4, wherein in said compound of formula I, said lower alkyl has between 1 and 4 carbon atoms.

6. A composition according to claim 4, wherein said compound of formula I is selected from the group consisting of:
N-(2-butyl)-N-methylpropargylamine hydrochloride,
N-(2-butyl)-N-methylpropargylamine oxalate,
N-(1-butyl)-N-methylpropargylamine hydrochloride,
N-(2-propyl)-N-methylpropargylamine hydrochloride,
N-(1-pentyl)-N-methylpropargylamine hydrochloride,
N-(2-pentyl)-N-methylpropargylamine hydrochloride,
N-(2-pentyl)-N-methylpropargylamine oxalate,
N-(2-decyl)-N-methylpropargylamine hydrochloride,
N-(2-dodecyl)-N-methylpropargylamine hydrochloride,
N-(1-heptyl)-N-methylpropargylamine hydrochloride, and
N-(2-heptyl)-N-methylpropargylamine hydrochloride.

7. A method for the treatment of Parkinson's disease through in vivo inhibition of MAO-B, said method comprising administering to a patient in need thereof an effective amount of a MAO-B inhibitor having the following formula:

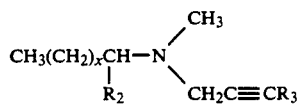

wherein
x represents an integer ranging from 1 to 13;
$R_2$ and $R_3$ are the same or different and represent H or a straight chain or branched lower alkyl,
and pharmaceutically acceptable salts thereof, in admixture with a pharmaceutically acceptable carrier, excipient or adjuvant.

8. A method according to claim 7, wherein in said compound of formula I, said lower alkyl has between 1 and 4 carbon atoms and wherein said halogen is selected from the group consisting of fluorine, chlorine, bromine and iodine.

9. A method according to claim 7, wherein said compound according to formula I is selected from the group consisting of:
N-(2-butyl)-N-methylpropargylamine hydrochloride,
N-(2-butyl)-N-methylpropargylamine oxalate,
N-(1-butyl)-N-methylpropargylamine hydrochloride,
N-(2-propyl)-N-methylpropargylamine hydrochloride,
N-(1-pentyl)-N-methylpropargylamine hydrochloride,
N-(2-pentyl)-N-methylpropargylamine hydrochloride,
N-(2-pentyl)-N-methylpropargylamine oxalate,
N-(2-decyl)-N-methylpropargylamine hydrochloride, N-(2-dodecyl)-N-methylpropargylamine hydrochloride,
N-(1-heptyl)-N-methylpropargylamine hydrochloride, and
N-(2-heptyl)-N-methylpropargylamine hydrochloride.

10. A method for the selective in vivo inhibition of MAO-B in humans, said method comprising administering to a subject an effective amount of a compound having the formula I:

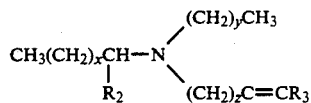

wherein
X represents an integer ranging from 1 to 13;
Y represents an integer ranging from 0 to 5;
Z represents an integer ranging from 0 to 5; $R_1$, $R_2$ and $R_3$ is the same or different and represent H or a straight chain or branched lower alkyl; and pharmaceutically acceptable salts thereof, in admixture with a pharmaceutically acceptable carrier, excipient or adjuvant.

11. A method according to claim 10, wherein in said compound of formula I, said lower alkyl has between 1 and 4 carbon atoms.

12. A method according to claim 10, wherein said compound according to formula I is selected from the group consisting of:
N-(2-butyl)-N-methylpropargylamine hydrochloride,
N-(2-butyl)-N-methylpropargylamine oxalate,
N-(1-butyl)-N-methylpropargylamine hydrochloride,
N-(2-propyl)-N-methylpropargylamine hydrochloride,
N-(1-pentyl)-N-methylpropargylamine hydrochloride,
N-(2-pentyl)-N-methylpropargylamine hydrochloride,
N-(2-pentyl)-N-methylpropargylamine oxalate,
N-(2-decyl)-N-methylpropargylamine hydrochloride,
N-(2-dodecyl)-N-methylpropargylamine hydrochloride,
N-(1-heptyl)-N-methylpropargylamine hydrochloride, and
N-(2-heptyl)-N-methylpropargylamine hydrochloride.

* * * * *

UNITED STATES PATENT AND TRADEMARK OFFICE
CERTIFICATE OF CORRECTION

PATENT NO. : 5,169,868  Page 1 of 2
DATED : December 8, 1992
INVENTOR(S) : Yu et al It is certified that error appears in the above-indentified patent and that said Letters Patent is hereby corrected as shown below:

Column 15, line 50, after "formula I:" insert:

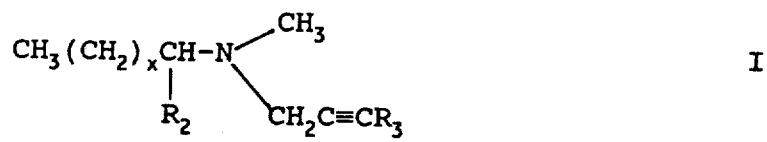         I

UNITED STATES PATENT AND TRADEMARK OFFICE
CERTIFICATE OF CORRECTION

PATENT NO. : 5,169,868

DATED : December 8, 1992

INVENTOR(S) : Yu et al

It is certified that error appears in the above-indentified patent and that said Letters Patent is hereby corrected as shown below:

Column 16, line 7, after "formula I:" insert:

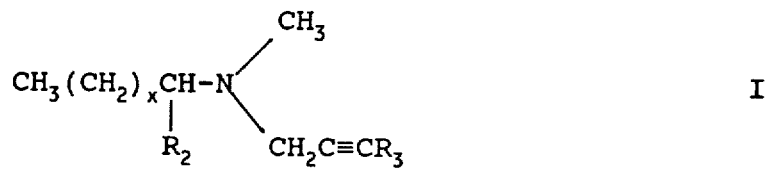

Signed and Sealed this

Eighth Day of February, 1994

Attest:

BRUCE LEHMAN

Attesting Officer    Commissioner of Patents and Trademarks